(12) United States Patent
Takechi et al.

(10) Patent No.: US 10,868,339 B2
(45) Date of Patent: Dec. 15, 2020

(54) AQUEOUS ELECTROLYTES WITH BIS(FLUOROSULFONYL)IMIDE SALT ELECTROLYTE AND IONIC LIQUID SYSTEM AND BATTERIES USING THE ELECTROLYTE SYSTEM

(71) Applicant: Toyota Motor Engineering & Manufacturing North America, Inc., Erlanger, KY (US)

(72) Inventors: Kensuke Takechi, Aichi (JP); Ruidong Yang, Wilmington, DE (US)

(73) Assignee: Toyota Motor Engineering & Manufacturing North America, Inc., Erlanger, KY (US)

(*) Notice: Subject to any disclaimer, the term of this patent is extended or adjusted under 35 U.S.C. 154(b) by 282 days.

(21) Appl. No.: 15/831,781

(22) Filed: Dec. 5, 2017

(65) Prior Publication Data

US 2019/0173131 A1    Jun. 6, 2019

(51) Int. Cl.

| | |
|---|---|
| *H01M 10/26* | (2006.01) |
| *H01M 4/131* | (2010.01) |
| *H01M 4/58* | (2010.01) |
| *C07F 9/54* | (2006.01) |
| *C07D 233/54* | (2006.01) |
| *C07C 211/62* | (2006.01) |
| *C07D 231/10* | (2006.01) |

(52) U.S. Cl.
CPC ........... *H01M 10/26* (2013.01); *C07F 9/5407* (2013.01); *H01M 4/131* (2013.01); *H01M 4/5815* (2013.01); *C07C 211/62* (2013.01); *C07D 231/10* (2013.01); *C07D 233/54* (2013.01); *C07F 9/54* (2013.01); *H01M 2220/20* (2013.01); *H01M 2300/0014* (2013.01)

(58) Field of Classification Search
CPC .... H01M 10/26; H01M 4/131; H01M 4/5815; H01M 4/485; H01M 2220/20; H01M 2300/0014; C07F 9/5407; C07F 9/54; C07D 233/54; C07D 231/62; C07C 211/62; B60L 50/64
See application file for complete search history.

(56) References Cited

U.S. PATENT DOCUMENTS

| | | | |
|---|---|---|---|
| 6,645,667 | B1 | 11/2003 | Iwamoto et al. |
| 8,597,828 | B2 | 12/2013 | Marinet et al. |
| 8,828,575 | B2 | 9/2014 | Visco et al. |

(Continued)

FOREIGN PATENT DOCUMENTS

| | | | |
|---|---|---|---|
| JP | 2013-197061 | * | 9/2013 |
| WO | WO 2016/084792 | * | 6/2016 |

(Continued)

*Primary Examiner* — Laura Weiner
(74) *Attorney, Agent, or Firm* — Oblon, McClelland, Maier & Neustadt, L.L.P.

(57) ABSTRACT

An aqueous electrolyte composition suitable for a lithium secondary battery is provided. The aqueous electrolyte composition contains water; lithium bis(fluorosulfonyl) imide (LiFSI); and an ionic liquid comprising an organic cation and a bis(fluorosulfonyl) imide anion (FSI); wherein the ionic liquid is a liquid at 20° C. A lithium secondary battery containing the aqueous electrolyte and a vehicle at least partially powered by the battery are also provided.

14 Claims, 7 Drawing Sheets

(56) References Cited

U.S. PATENT DOCUMENTS

| | | | |
|---|---|---|---|
| 2009/0123845 A1* | 5/2009 | Zaghib | H01M 10/0566 |
| | | | 429/303 |
| 2012/0028164 A1 | 2/2012 | Lee et al. | |
| 2015/0207180 A1 | 7/2015 | Bakenov | |
| 2016/0149267 A1 | 5/2016 | Badding et al. | |
| 2016/0351968 A1 | 12/2016 | Wang et al. | |
| 2017/0077557 A1 | 3/2017 | Zheng et al. | |
| 2018/0254152 A1* | 9/2018 | Matsuo | H01G 11/84 |
| 2018/0342773 A1* | 11/2018 | Singh | H01M 10/0568 |

FOREIGN PATENT DOCUMENTS

| | | | |
|---|---|---|---|
| WO | WO 2017/057603 | * | 4/2017 |
| WO | WO 2017/105578 A2 | | 6/2017 |

* cited by examiner

AQUEOUS ELECTROLYTES WITH BIS(FLUOROSULFONYL)IMIDE SALT ELECTROLYTE AND IONIC LIQUID SYSTEM AND BATTERIES USING THE ELECTROLYTE SYSTEM

BACKGROUND

Field of the Disclosure

This disclosure is directed an aqueous electrolyte composition suitable for use in high energy batteries, including lithium ion secondary batteries, which provides a wide electrochemical window of performance and increased safety and convenience in vehicle construction.

Discussion of the Background

A demand of intrinsically safe high-energy batteries is now urgent because of the rapid development and commercialization of electrified vehicles such as EV, PHV and HV. Since the current Li-ion secondary battery contains a flammable non-aqueous electrolyte, it is necessary to install external battery control circuits and internal safety components in the vehicle. On the other hand, batteries using aqueous (water-based) electrolyte, such as Ni-MH battery, are much safer because of the inflammable property of the electrolyte, however, the energy density of batteries with aqueous electrolytes is quite low due to a low voltage profile resulting from the limited electrochemical stability of the aqueous electrolyte. In conventional aqueous electrolytes, the electrochemical stability (electrochemical window) determined by the decomposition voltage of the water is usually less than 2 V.

Thus, aqueous electrolyte batteries known to date do not provide the energy density necessary to compete with or replace current Li-ion batteries, because the electrochemical stability of the aqueous electrolyte has such a low voltage profile. One effort to widen the electrochemical window by suppression of the decomposition has included preparing a highly concentrated aqueous electrolyte composition and such systems may perform with an electrochemical window as wide as about 3 V. In one system for a lithium-ion battery electrolyte the composition contains a high concentration of a Li-salt (21m) which is believed to stabilize the water by formation of a complex between the salt and the water molecule. Since the window of the free-water (bulk water, regular water), which has clusters of water molecules, is different from the window of individual water molecules, the water molecules coordinated by highly concentrated salt ions can behave like the "individual water molecules" to have a wider electrochemical window.

However, the limit of the reduction (negative) voltage of the window of such systems is about 1.8 V (vs Li/Li+) and this value of reducing voltage limits the candidates suitable for utility as anode materials. For example, one anode material presently of high interest, lithium titanium oxide ($Li_4Ti_5O_{12}$) (LTO), would not be suitable in such a battery system because the redox potential of LTO is about 1.5 V.

Accordingly, one object of the present invention is to provide an aqueous electrolyte composition having an electrochemical window sufficiently wide to be compatible and functional in a secondary battery having anode and cathode materials which provide high energy density.

Another object of the present invention is to provide an aqueous electrolyte system for a lithium-ion secondary battery having an electrochemical window sufficiently wide to be compatible and functional in a secondary battery having anode and cathode materials which provide high energy density.

A further object of the invention is to provide a lithium ion secondary battery having an aqueous electrolyte which has an energy density equal to or greater than present conventional lithium-ion batteries.

SUMMARY OF THE DISCLOSURE

These and other objects have been achieved by the present disclosure, the first embodiment of which includes an aqueous electrolyte for a lithium-ion secondary battery comprising: water; lithium bis(fluorosulfonyl) imide (LiFSI); and an ionic liquid comprising an organic cation and a bis(fluorosulfonyl) imide anion (FSI); wherein the ionic liquid is a liquid at 20° C.

In an aspect of the first embodiment, the organic cation of the ionic liquid is selected from the group consisting of an alkyl-ammonium cation, an alkylpiperidinium cation, an alkylpyrrolidinium cation, an alkylimidazolium cation and an alkylphosphonium cation.

In another aspect of the first embodiment the aqueous electrolyte further comprises a lithium salt of an anion comprising a fluoroalkylsulfonyl group of formula (I):

$$R-SO_2- \qquad (I)$$

wherein R is a perfluoroalkyl group of 1-5 carbons; wherein a molar ratio of the lithium fluoroalkylsulfonyl group anion salt to total moles of LiFSI and the lithium fluoroalkylsulfonyl group anion salt is less than ½.

In a second embodiment the present disclosure includes a lithium secondary battery comprising: an anode capable of intercalation and de-intercalation of lithium ions; a cathode capable of intercalation and de-intercalation lithium ions; and an aqueous electrolyte in contact with the anode and cathode which comprises: water; lithium bis(fluorosulfonyl) imide (LiFSI); and an ionic liquid comprising an organic cation and a bis(fluorosulfonyl) imide anion (FSI); wherein the ionic liquid is a liquid at 20° C.

In an aspect of the second embodiment the anode capable of intercalation and de-intercalation of lithium ions is stable to water and has a redox potential greater than 0.5 V vs Li/Li+.

In a further aspect of the second embodiment the cathode capable of intercalation and de-intercalation lithium ions comprises at least one compound selected from the group consisting of $LiMn_2O_4$, $LiCoO_2$, $LiFe_2(PO_4)$, $LiMn_{1/3}Ni_{1/3}Co_{1/3}O_2$, $LiNi_{0.5}Mn_{1.5}O_4$ and $LiCoPO_4$.

In a third embodiment a vehicle having a battery of the second embodiment is provided.

The foregoing description is intended to provide a general introduction and summary of the present disclosure and is not intended to be limiting in its disclosure unless otherwise explicitly stated. The presently preferred embodiments, together with further advantages, will be best understood by reference to the following detailed description taken in conjunction with the accompanying drawings.

DETAILED DESCRIPTION OF THE DISCLOSURE

Within the description of this disclosure, all cited references, patents, applications, publications and articles that are under authorship, joint authorship or ascribed to members of the Assignee organization are incorporated herein by reference. Where a numerical limit or range is stated, the endpoints are included. Also, all values and subranges within a numerical limit or range are specifically included as if explicitly written out. As used herein, the words "a" and "an" and the like carry the meaning of "one or more." The phrases "selected from the group consisting of," "chosen from," and the like include mixtures of the specified materials. Terms such as "contain(s)" and the like are open terms meaning 'including at least' unless otherwise specifically noted. Where % composition description is provided the % values are % by weight unless specified otherwise. As used herein, the term "vehicle" refers to any power driven device designed for transportation including an automobile, truck van, bus, golf cart and other utility forms of transportation.

In ongoing investigation to further widen the electrochemical window and safety of lithium-ion batteries, the inventors are conducting extensive studies of aqueous electrolyte systems and methods to widen the electrochemical window thereof. In U.S. application Ser. No. 15/252,513, filed Aug. 31, 2016, the present inventors disclosed that the water component of an electrolyte system may be strongly stabilized in a composition containing a chemical component in addition to a concentrated salt. Explicitly, it was described that a highly stabilized electrolyte system for a lithium-ion battery having a wide electrochemical window may be obtained by including a lithium salt of an anion having a fluoroalkylsulfonyl group and linear or cyclic ether in the aqueous composition.

In continuing studies of aqueous electrolyte systems as described in copending U.S. application Ser. No. 15/663, 262, filed Jul. 28, 2017, the inventors further discovered that a lithium ion electrolyte system may be extensively stabilized and the electrochemical window broadened with an aqueous electrolyte comprising: water; a lithium salt of an anion comprising a fluoroalkylsulfonyl group of formula (I):

R—SO₂—        (I)

wherein R is a perfluoroalkyl group of 1-5 carbons; and an ionic liquid which is a salt of a protonic cation and an anion comprising a fluoroalkylsulfonyl group of formula (I).

Figure 2:
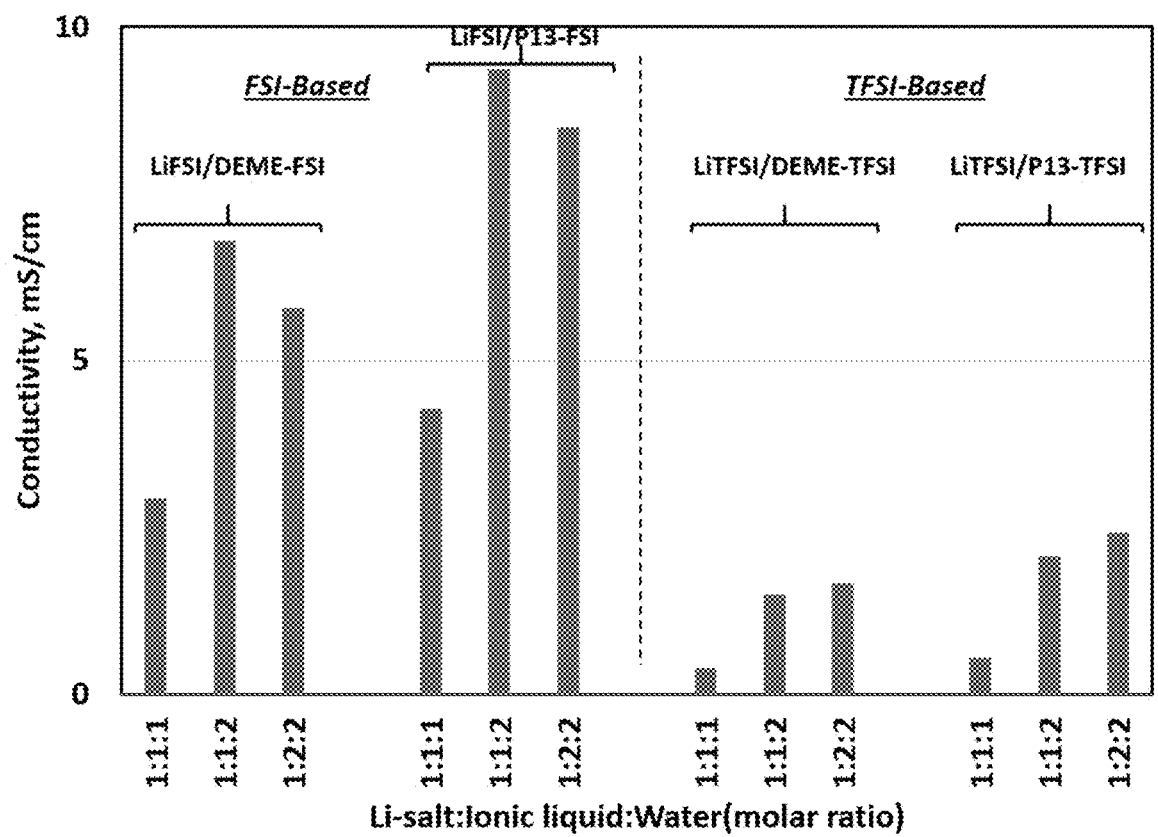
FIG. 2 shows a conductivity comparison between FSI- and TFSI-based electrolytes.
Figure 3:
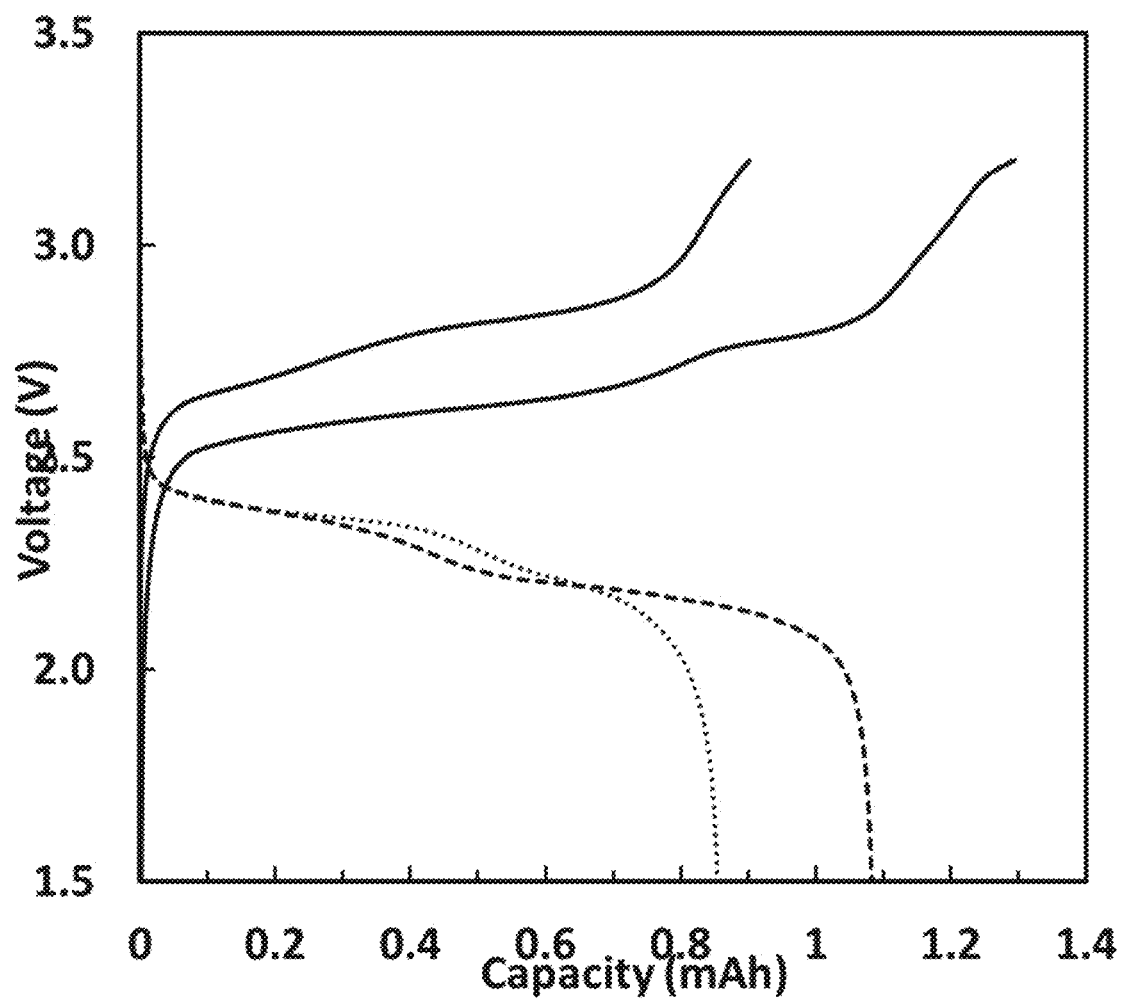
FIG. 3 shows the charge/discharge curves (1$^{st}$ and the 10$^{th}$ cycles) of a battery (LMO/LTO) with Example 1 electrolyte.
Figure 4:
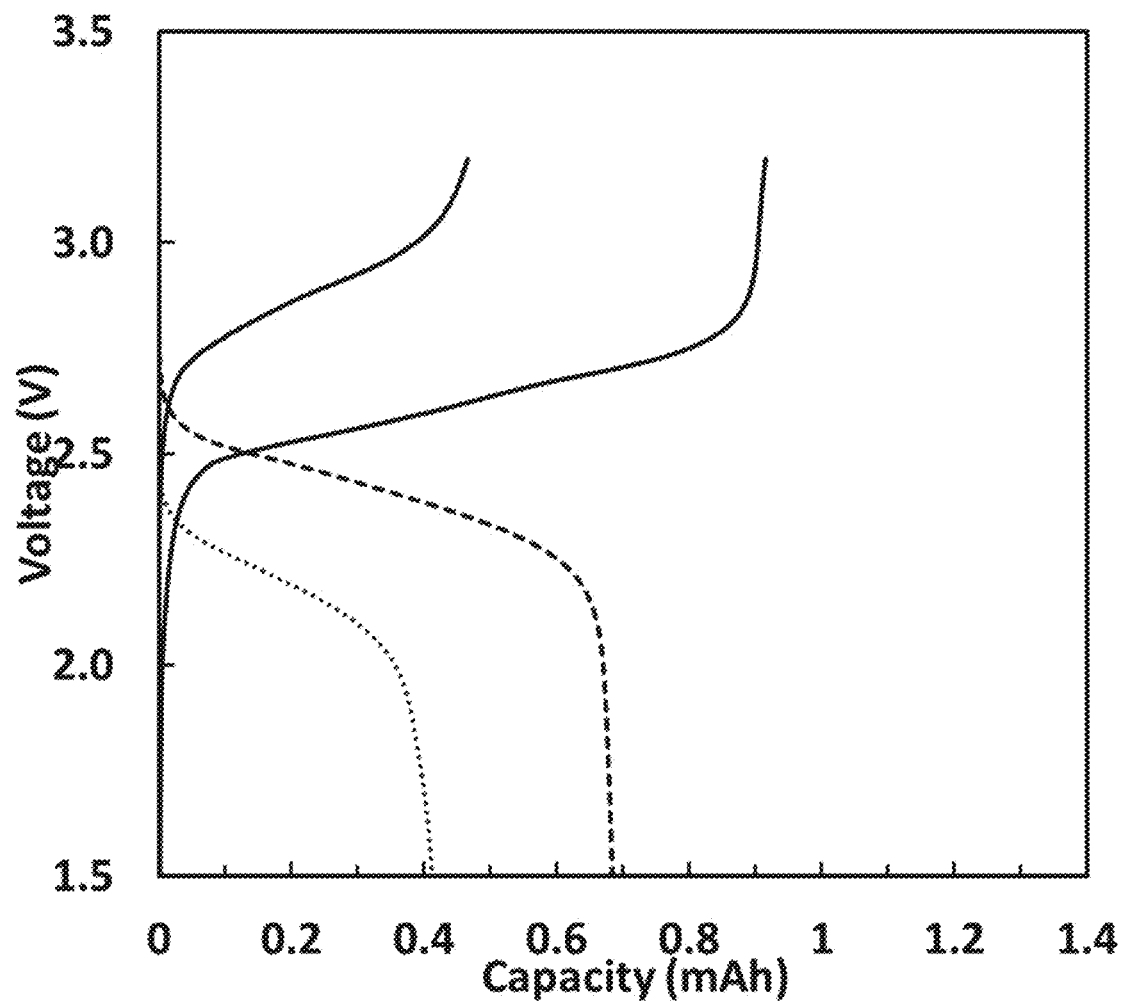
FIG. 4 shows the charge/discharge curves ($1^{st}$ and the $10^{th}$ cycles) of a battery (LMO/LTO) with Example electrolyte 2.
Figure 5:
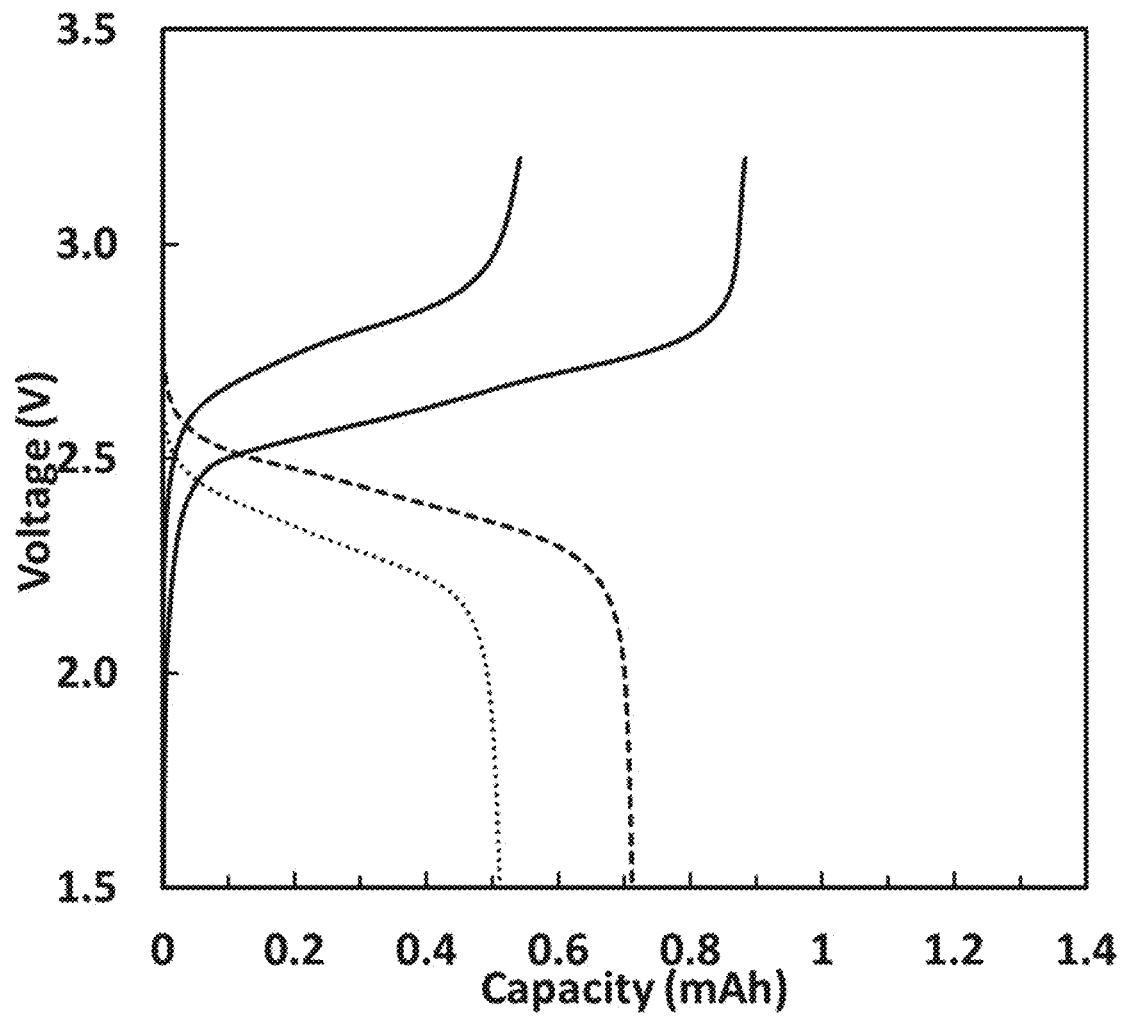
FIG. 5 shows the charge/discharge curves ($1^{st}$ and the $10^{th}$ cycles) of a battery (LMO/LTO) with Example electrolyte 3.
Figure 6:
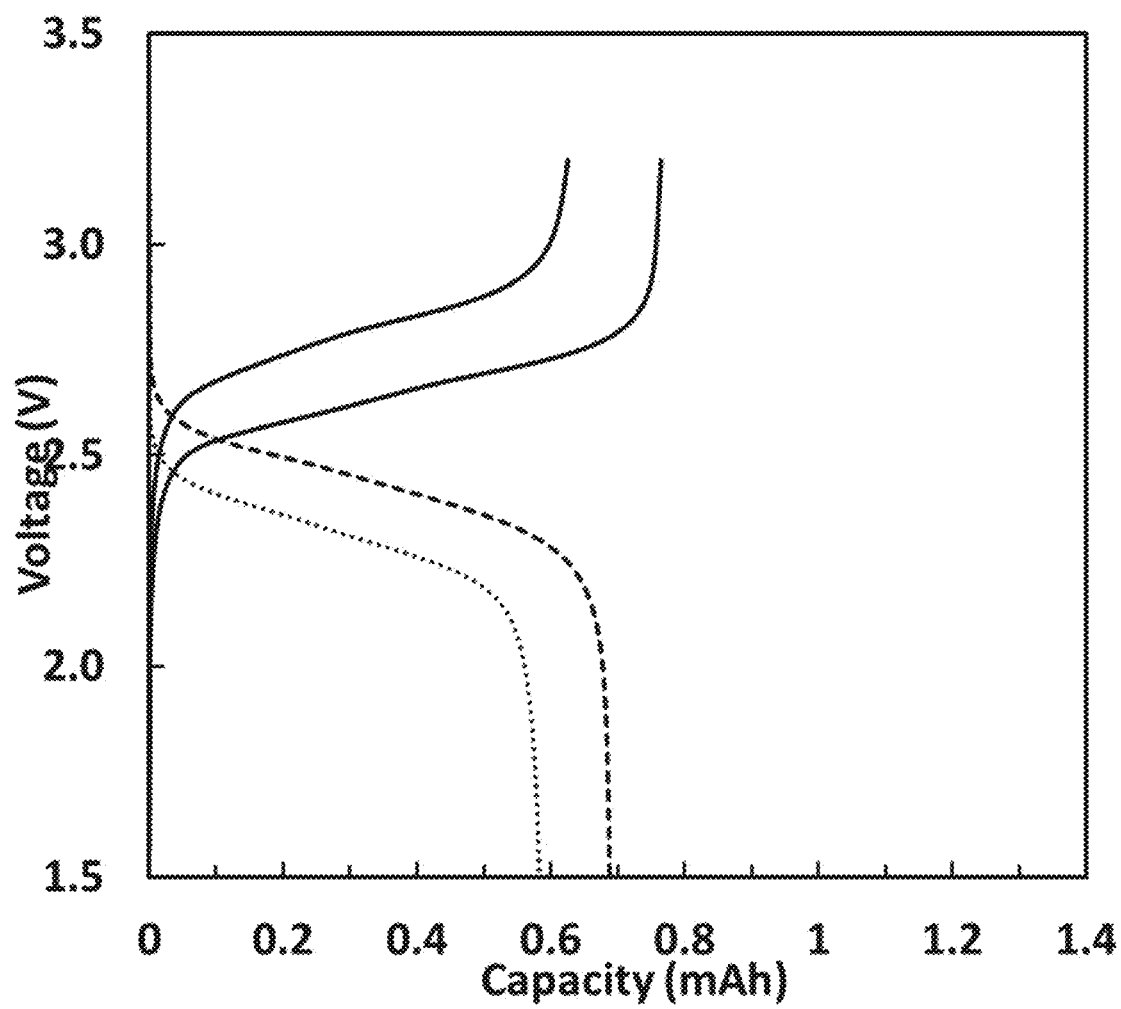
FIG. 6 shows the charge/discharge curves ($1^{st}$ and the $10^{th}$ cycles) of a battery (LMO/LTO) with Example electrolyte 4.
Figure 7:
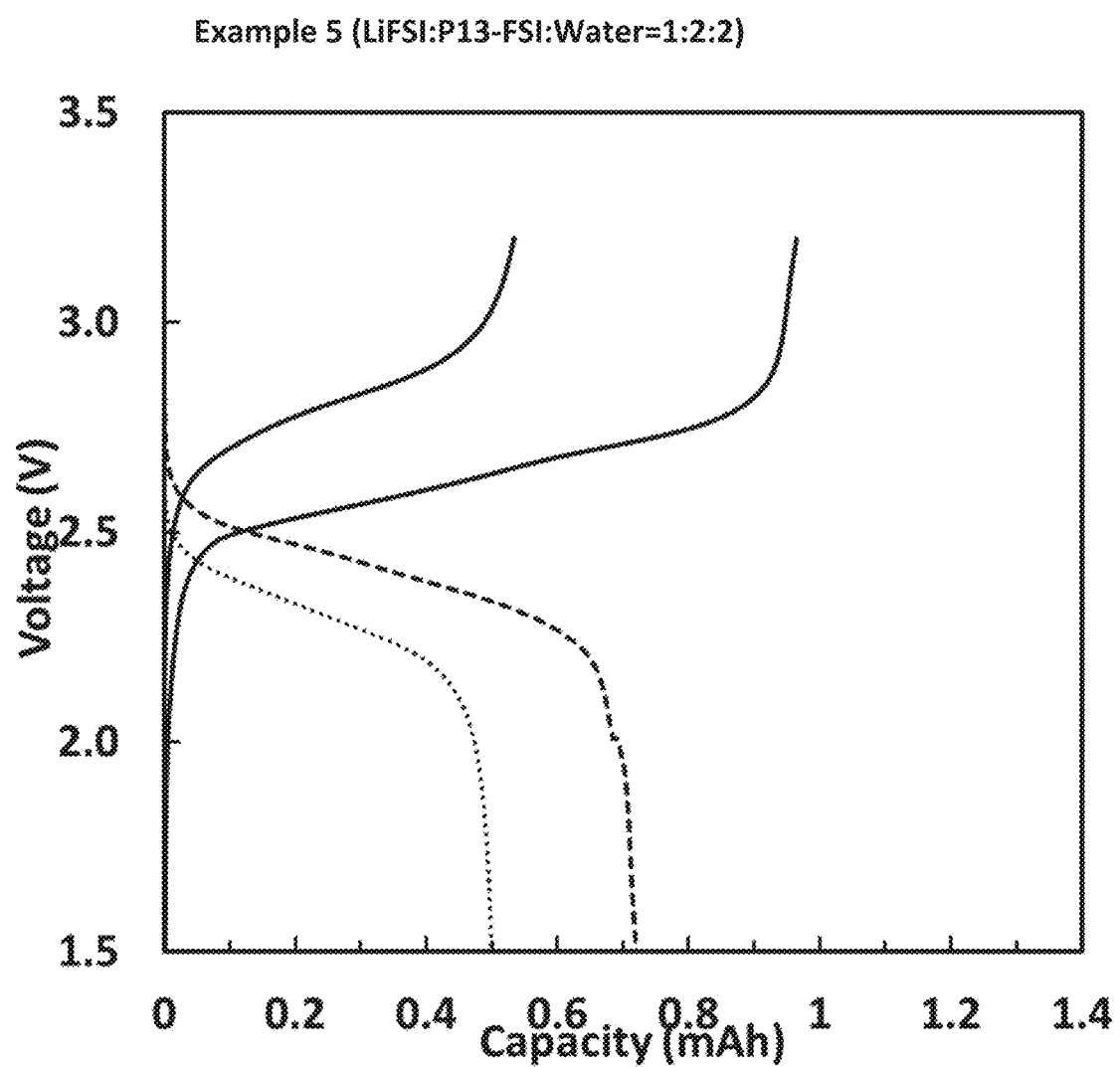
FIG. 7 shows the charge/discharge curves ($1^{st}$ and the $10^{th}$ cycles) of a battery (LMO/LTO) with Example electrolyte 6.

In ongoing efforts to further improve and extend the performance range of lithium secondary batteries the inventors have surprisingly and unexpectedly discovered that the above objectives are even more achieved with an aqueous electrolyte system based upon bis(fluorosulfonyl) imide (FSI) systems as described in the present application. As shown in FIG. 2 the FSI electrolyte systems according to the following embodiments show significantly higher conductivity than systems previously described. Further as shown in FIGS. 3-7, lithium secondary batteries containing the electrolyte system of the following embodiments provide high discharge voltage over 2V while maintaining stable cycling performance.

Thus, in a first embodiment an aqueous electrolyte for a lithium-ion secondary battery is provided. The aqueous electrolyte comprises: water; lithium bis(fluorosulfonyl) imide (LiFSI); and an ionic liquid comprising an organic cation and a bis(fluorosulfonyl) imide anion (FSI); wherein the ionic liquid is a liquid at 25° C., preferably 20° C. and most preferably 18° C. Thus the ionic liquid may be described as a room temperature ionic liquid (RTIL).

The organic cation of the ionic liquid may be selected from the group consisting of alkyl-ammonium cations, alkylpiperidinium cations, alkylpyrrolidinium cations, alkylimidazolium cations and an alkylphosphonium cation. According to the present embodiments the term alkyl is defined as a linear, branched, cyclic or alicyclic hydrocarbon group having 1 to 18 carbon atoms, preferably 1-12 carbon atoms and most preferably 1-6 carbon atoms. One of ordinary skill recognizes that when the molecular weight of the ionic liquid is increased to a structurally defined value the ionic compound is no longer liquid at room temperature (20-25° C.). When multiple alkyl groups are present in the cation structure, each is independent of the other and the alkyl group may optionally contain an ether oxygen in the carbon chain.

Examples of cationic ions according to the present embodiments include but are not limited to a cation is selected from the group consisting of formulae (I), (II), (III), (IV) and (V) and mixtures thereof:

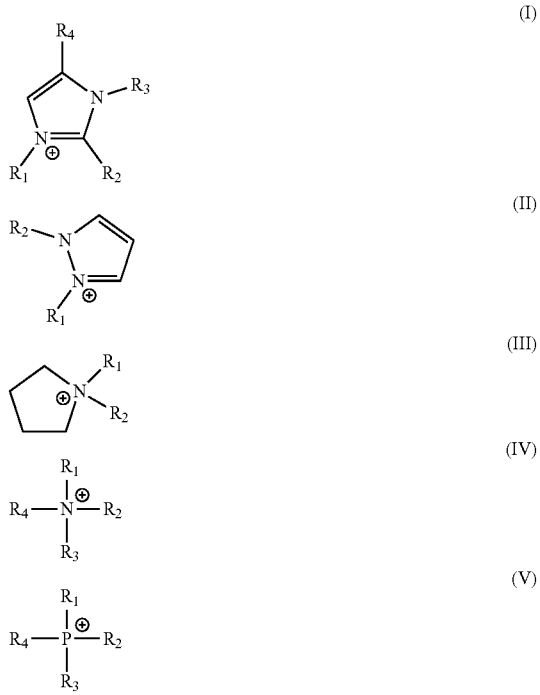

Groups $R_1$ to $R_4$ may each independently be —H or an alkyl group as previously defined, with the proviso that at least one of $R_1$ to $R_4$ must be alkyl.

Examples of cations suitable for the RTIL of the present embodiments include but are not limited to N-methyl-N-propylpyrrolidinium(P13) FSI, N-methyl-N-butylpyrrolidinium(P14) FSI. N-methyl-N-propylpiperidinium(PP13)

FSI, N-methyl-N-butylpiperidinium(PP14) FSI, Trimethylpropylammonium(N1113) FSI, Diethylmethyl(2-methoxyethyl)ammonium(DEME) FSI and Methyl(tri-n-butyl)phosphonium(P1444) FSI.

In one aspect of the first embodiment a mole ratio of the lithium bis(fluorosulfonyl) imide (LiFSI), water and the ionic liquid is such that for 1 mole of the LiFSI, there are 0.1 to mole, preferably 0.25 to 10 mole of the ionic liquid and 0.1 to 10 mole, preferably 0.25 to mole of water. These ranges include all subrange ratios within the broader ranges.

A molar content of the LiFSI in the aqueous electrolyte may be from 2 M to 20 M, preferably from 3 M to 15 M and most preferably from 4 M to 12 M.

In another aspect of the first embodiment, the electrolyte may further contain a lithium salt different from the LiFSI. According to this aspect the lithium salt different from LiFSI may be one or more lithium salts of an anion comprising a fluoroalkylsulfonyl group of formula (I):

R—SO$_2$— (I)

wherein R is a perfluoroalkyl group of 1-5 carbons. However, when one or more salts different from LiFSI are included, a total mole content of the one or more different salts may have a molar ratio of the lithium fluoroalkylsulfonyl group anion salt to total moles of LiFSI and the lithium fluoroalkylsulfonyl group anion salt is less than ½. Further when one or more salts different from LiFSI are included a total concentration of the LiFSI and the lithium fluoroalkylsulfonyl group anion salt is from 2 M to 20 M, preferably from 3 M to 15 M and most preferably from 4 M to 12 M.

Nonlimiting examples of suitable lithium salts include lithium bis(trifluoromethyl-sulfonyl)imide (LiTFSI), lithium bis(pentafluoroethyl-sulfonyl)imide (LiBETI), lithium bis(fluoromethylsulfonyl)imide (LiFSI) and lithium trifluoromethylsulfonate (LiTFS).

The inventors have discovered that water stabilization is significantly enhanced with the electrolyte compositions according the embodiments and aspects described in this application. Thus a wide electrochemical window may be obtained which allows for utilization of Lithium Nickel Manganese Oxide (Li Ni$_{0.5}$Mn$_{1.5}$O$_4$, "LNMO") as well as LTO or other conventional Li$^+$ anode materials). Importantly, the electrolyte liquids of this first embodiment may have good fluidity and good conductivity as shown in FIG. 2.

In a second embodiment an aqueous lithium secondary battery is provided. The battery comprises: an anode capable of intercalation and de-intercalation of lithium ions; a cathode capable of intercalation and de-intercalation lithium ions; and an aqueous electrolyte in contact with the anode and cathode which comprises: water; lithium bis(fluorosulfonyl) imide (LiFSI); and an ionic liquid comprising an organic cation and a bis(fluorosulfonyl) imide anion (FSI); wherein the ionic liquid is a liquid at 20° C.

According to the second embodiment the organic cation of the ionic liquid is selected from the group consisting of an alkyl-ammonium cation, an alkylpiperidinium cation, an alkylpyrrolidinium cation, an alklimidazolium cation and an alkylphosphonium cation. The previous discussion of "alkyl" group is incorporated in this embodiment.

Examples of cationic ions according to the present embodiments include but are not limited to a cation is selected from the group consisting of formulae (I), (II), (III), (IV) and (V):

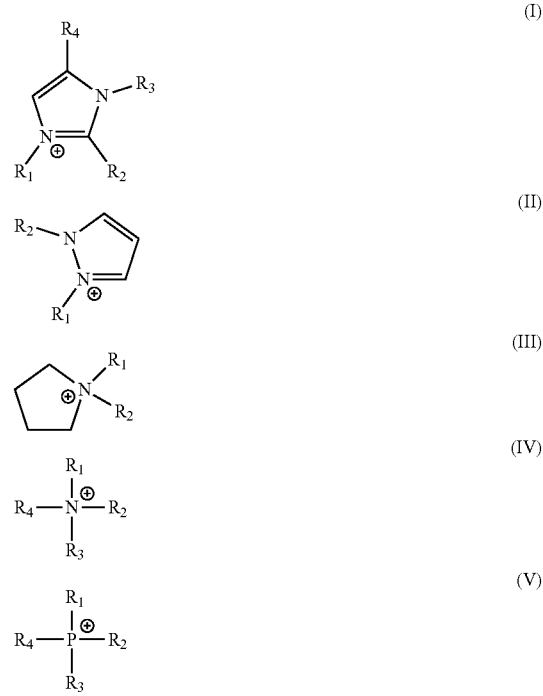

Groups $R_1$ to $R_4$ may each independently be —H or an alkyl group as previously defined, with the proviso that at least one R group must be alkyl.

Examples of cations suitable for the RTIL of the lithium secondary battery include but are not limited to N-methyl-N-propylpyrrolidinium(P13) FSI, N-methyl-N-butylpyrrolidinium(P14) FSI, N-methyl-N-propylpiperidinium(PP13) FSI, N-methyl-N-butylpiperidinium(PP14) FSI, Trimethylpropylammonium(N1113) FSI, Diethylmethyl(2-methoxyethyl)ammonium(DEME) FSI and Methyl(tri-n-butyl)phosphonium(P1444) FSI.

In one aspect of the second embodiment a mole ratio of the lithium bis(fluorosulfonyl) imide (LiFSI), water and the ionic liquid in the secondary battery is such that for 1 mole of the LiFSI, there are 0.1 to 20 mole, preferably 0.25 to 10 mole of the ionic liquid and 0.1 to 10 mole, preferably 0.25 to 5 mole of water. These ranges include all subrange ratios within the broader ranges.

A molar content of the LiFSI in the aqueous electrolyte may be from 2 M to 20 M, preferably from 3 M to 15 M and most preferably from 4 M to 12 M.

In another aspect of the second embodiment, the electrolyte may further contain a lithium salt different from the LiFSI. According to this aspect the lithium salt different from LiFSI may be one or more lithium salts of an anion comprising a fluoroalkylsulfonyl group of formula (I):

R—SO$_2$— (I)

wherein R is a perfluoroalkyl group of 1-5 carbons. However, when one or more salts different from LiFSI are included, a total mole content of the one or more different salts may have a molar ratio of the lithium fluoroalkylsulfonyl group anion salt to total moles of LiFSI and the lithium fluoroalkylsulfonyl group anion salt is less than ½. Further when one or more salts different from LiFSI are included a total concentration of the LiFSI and the lithium fluoroalkylsulfonyl group anion salt is from 2 M to 20 M, preferably from 3 M to 15 M and most preferably from 4 M to 12 M.

Nonlimiting examples of suitable lithium salts different from LiFSI include lithium bis(trifluoromethyl-sulfonyl)imide (LiTFSI), lithium bis(pentafluoroethyl-sulfonyl)imide (LiBETI), lithium bis(fluoromethylsulfonyl)imide (LiFSI) and lithium trifluoromethylsulfonate (LiTFS).

Aqueous rechargeable lithium ion batteries (ARLB) must contain electrodes stable and compatible with water. Generally, any material capable of intercalation and de-intercalation of Li ions which is stable to exposure to water under electrochemical conditions may be employed.

Suitable cathode materials which are compatible with an aqueous electrolyte and have an appropriate redox potential of less than 5.5 V vs Li/Li+ include but are not limited to: $LiMn_2O_4$, $LiCoO_2$, $LiFe_2(PO_4)$, $LiMn_{1/3}Ni_{1/3}Co_{1/3}O_2$, $LiNi_{0.5}Mn_{1.5}O_4$ and $LiCoPO_4$. Porous forms of any these may be prepared and nanoparticle structure may be especially useful as active cathode materials.

The cathode may be prepared by mixing the particles according to at least one the above materials with one or more binders and other materials conventionally employed to prepare a cathode structure for an aqueous electrolyte system. These materials may be mixed as a slurry, coated onto a metal foil, and dried. The methods of construction of a cathode employing an active material are conventionally known and any such method that is compatible with the particles of the disclosure may be employed.

Suitable binders known to one of ordinary skill which are chemically stable in the potential window of use of the cell may include thermoplastics and thermosetting resins. For example, polyethylene, polypropylene, polytetrafluoroethylene (PTFE), polyvinylidene fluoride (PVDF), styrene butadiene rubber, a tetrafluoroethylene hexafluoro ethylenic copolymer, a tetrafluoroethylene hexafluoropropylene copolymer (FEP), a tetrafluoroethylene perfluoroalkyl vinyl ether copolymer (PFA), ethylene-tetrafluoroethylene copolymer (ETFE resin), polychlorotrifluoroethylene resin (PCTFE), a propylene-tetrafluoroethylene copolymer, an ethylene-chlorotrifluoroethylene copolymer (ECTFE) and an ethylene-acrylic acid copolymer. These binders may be used independently, or mixtures may be used.

The components may be wet blended in the presence of a suitable solvent or dry blended using a mortar or other conventionally known mixing equipment. The mixture may then be applied to a charge collector by conventionally known methods. Any suitable charge collector may be employed. Preferred charge collectors may be any of carbon, stainless steel, nickel, aluminum and copper.

The cathode thus prepared may be employed in the construction of an aqueous lithium-ion battery in a conventionally known manner.

With regard to the anode any kind of material suitable for utility in a Li-ion battery, which is compatible with aqueous electrolyte and has appropriate redox potential (greater than 0.5 V vs Li/Li+) may be employed. Suitable examples include, but are not limited to $Li_4Ti_5O_{12}$, elemental sulfur, $Mo_6S_8$, $Cu_2V_2O_7$, $TiS_4$, $NbS_5$ and Li terephthalate. Porous forms of any these may be prepared and nanoparticle structure may be especially useful.

The anode may be prepared by mixing the particles according to at least one the above anode materials with one or more binders and other materials conventionally employed to prepare an anode structure for an aqueous electrolyte system. These materials may be mixed as a slurry, coated onto a metal foil, and dried. The methods of construction of a anode employing an active material are conventionally known and any such method that is compatible with the particles of the disclosure may be employed.

Suitable binders known to one of ordinary skill which are chemically stable in the potential window of use of the cell may include thermoplastics and thermosetting resins. For example, polyethylene, polypropylene, polytetrafluoroethylene (PTFE), polyvinylidene fluoride (PVDF), styrene butadiene rubber, a tetrafluoroethylene hexafluoro ethylenic copolymer, a tetrafluoroethylene hexafluoropropylene copolymer (FEP), a tetrafluoroethylene perfluoroalkyl vinyl ether copolymer (PFA), ethylene-tetrafluoroethylene copolymer (ETFE resin), polychlorotrifluoroethylene resin (PCTFE), a propylene-tetrafluoroethylene copolymer, an ethylene-chlorotrifluoroethylene copolymer (ECTFE) and an ethylene-acrylic acid copolymer. These binders may be used independently, or mixtures may be used.

The components may be wet blended in the presence of a suitable solvent or dry blended using a mortar or other conventionally known mixing equipment. The mixture may then be applied to a charge collector by conventionally known methods. Any suitable charge collector may be employed. Preferred charge collectors may be any of carbon, stainless steel, nickel, aluminum and copper.

The battery further comprises a separator between the anode and cathode and any type of conventionally known separator compatible with an aqueous electrolyte may be employed.

The battery may be enclosed in a container and multiple units may be combined to form a battery as is conventionally known.

Figure 1:
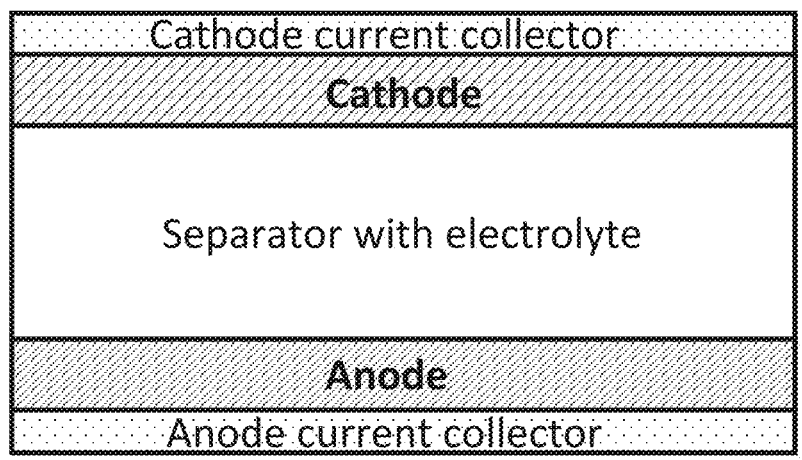
FIG. 1 shows a battery cell configuration employed for evaluation of the electrolyte systems of the Examples.

Preparation and charge/discharge performance evaluation of batteries according to an embodiment as shown in FIG. 1 are described in Examples 1 to 6 below. The charge discharge curves for Examples 1-4 and 6 are shown in FIGS. 3 to 7 and as indicated the batteries are stable over the cycles demonstrated and have good capacity.

In further embodiments the present disclosure includes a vehicle containing the battery according to the present disclosure wherein the vehicle includes an automobile, truck van, bus, golf cart and other utility forms of transportation.

Having generally described this disclosure, a further understanding can be obtained by reference to certain specific examples which are provided herein for purposes of illustration only and are not intended to be limiting unless otherwise specified.

EXPERIMENTAL

Coin cell batteries of the 2032-type shown schematically in FIG. 1 were prepared with a cathode having in an active layer of $LiMn_2O_4$(LMO) and conductive carbon with a PVdF binder. The anodes were prepared with $Li_4Ti_5O_{12}$ and conductive carbon with a PVdF binder. A Separator constructed of a Glass fiber separator was placed between the anode and cathode. The electrolyte composition for each Example is shown in the following Table. To evaluate charge/discharge performance of the battery the battery was first charged at 1.0 mA/cm$^2$ to a cut-off of 3.2 V. The battery was then discharged at 1.0 mA/cm$^2$ to a cut-off of 1.5 V. The temperature for the evaluation was 25° C.

| Electrolyte Example | Lithium salt (molar ratio) | Ionic Liquid (molar ratio) | Water (molar ratio) |
|---|---|---|---|
| 1 | LiFSI (1) | DEME-FSI (1) | (1) |
| 2 | LiFSI (1) | DEME-FSI (1) | (2) |
| 3 | LiFSI (1) | DEME-FSI (2) | (2) |
| 4 | LiFSI (1) | P13-FSI (1) | (1) |

| Electrolyte Example | Lithium salt (molar ratio) | Ionic Liquid (molar ratio) | Water (molar ratio) |
|---|---|---|---|
| 5 | LiFSI (1) | P13-FSI (1) | (2) |
| 6 | LiFSI (1) | P13-FSI (2) | (2) |
| Comparative 1 | LiTFSI (1) | DEME-TFSI (1) | (1) |
| Comparative 2 | LiTFSI (1) | DEME-TFSI (1) | (2) |
| Comparative 3 | LiTFSI (1) | DEME-TFSI (2) | (2) |
| Comparative 4 | LiTFSI (1) | P13-TFSI (1) | (1) |
| Comparative 5 | LiTFSI (1) | P13-TFSI (1) | (2) |
| Comparative 6 | LiTFSI (1) | P13-TFSI (2) | (2) |

LiFSI—lithium bis(fluorosulfonyl) imide
LiTFSI—lithium bis(trifluoromethylsulfonyl)imide
DEME-FSI—Diethylmethyl(2-methoxyethyl)ammonium bis(fluorosulfonyl) imide
DEME-TFSI—Diethylmethyl(2-methoxyethyl)ammonium bis(trifluoromethylsulfonyl) imide
P13-FSI—N-methyl-N-propylpyrrolidinium bis(fluorosulfonyl) imide
P13-TFSI—N-methyl-N-propylpyrrolidinium bis(trifluoromethylsulfonyl)imide FIG. 2 shows the measured conductivity comparison between the FSI- and TFSI-based electrolytes. The figure shows clear evidence that the conductivities of the FSI-based electrolytes of Claim 1 are significantly higher than those of TFSI-based electrolytes in the same "salt/ionic liquid/water" ratio composition.

The charge/discharge curves ($1^{st}$ and the $10^{th}$ cycles) for batteries (LMO/LTO) with Example electrolytes 1-4 and 6 are shown in FIGS. 3-7. These figures show that the batteries according to Claim 8 perform high discharge voltage over 2 V with stable cycling.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. An aqueous electrolyte for a lithium-ion secondary battery comprising:
    water;
    lithium bis(fluorosulfonyl) imide (LiFSI); and
    an ionic liquid comprising an organic cation and a bis(fluorosulfonyl) imide anion (FSI);
    wherein
    the organic cation of the ionic liquid is selected from the group consisting of an alkyl-ammonium cation, an alkylpiperidinium cation, an alkylpyrrolidinium cation, an alkylimidazolium cation and an alkylphosphonium cation,
    a content of the LiFSI is from 3 M to 20 M,
    a mole ratio of the LiFSI, water and the ionic liquid is such that for 1 mole of the LiFSI, there are 0.1 to 20 mole of the ionic liquid and 0.1 to 10 mole water, and the ionic liquid is a liquid at 20° C.

2. The aqueous electrolyte for a lithium secondary battery according to claim 1, wherein the organic cation is selected from the group consisting of formulae (I), (II), (III), (IV) and (V) and mixtures thereof:

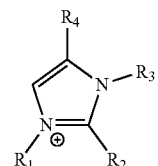
(I)

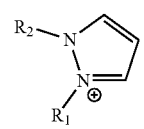
(II)

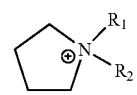
(III)

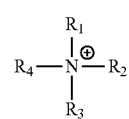
(IV)

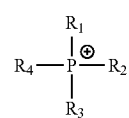
(V)

wherein $R_1$ to $R_4$ are each independently H or a linear, branched, cyclic or alicyclic hydrocarbon group having 1 to 18 carbon atoms, optionally substituted with an ether oxygen, with the proviso that at least one of $R_1$ to $R_4$ cannot be H.

3. The aqueous electrolyte for a lithium secondary battery according to claim 1, wherein a concentration of the LiFSI is from 4 M to 20 M.

4. The aqueous electrolyte for a lithium secondary battery according to claim 1, further comprising a lithium salt of an anion comprising a fluoroalkylsulfonyl group of formula (I):

R—SO2—     (I)

wherein R is a perfluoroalkyl group of 1-5 carbons;
wherein a molar ratio of the lithium fluoroalkylsulfonyl group anion salt to total moles of LiFSI and the lithium fluoroalkylsulfonyl group anion salt is less than ½.

5. The aqueous electrolyte for a lithium secondary battery according to claim 4, wherein a total concentration of the LiFSI and the lithium fluoroalkylsulfonyl group anion salt is from 3 M to 20 M.

6. A lithium secondary battery comprising:
    an anode capable of intercalation and de-intercalation of lithium ions;
    a cathode capable of intercalation and de-intercalation lithium ions; and
    an aqueous electrolyte according to claim 1 in contact with the anode and cathode.

7. The lithium secondary battery according to claim 6, wherein the cation is selected from the group consisting of formulae (I), (II), (III), (IV) and (V) and mixtures thereof:

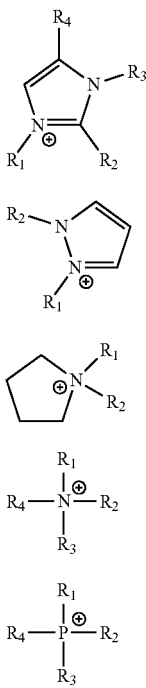

(I)

(II)

(III)

(IV)

(V)

wherein $R_1$ to $R_4$ are each independently H or a linear, branched, cyclic or alicyclic hydrocarbon group having 1 to 18 carbon atoms, optionally substituted with an ether oxygen, with the proviso that at least one of $R_1$ to $R_4$ cannot be H.

8. The lithium secondary battery according to claim 6, wherein a concentration of the LiFSI is from 4 M to 20 M.

9. The lithium secondary battery according to claim 6, further comprising a lithium salt of an anion comprising a fluoroalkylsulfonyl group of formula (I):

$$R-SO_2- \qquad (I)$$

wherein R is a perfluoroalkyl group of 1-5 carbons;
wherein a molar ratio of the lithium fluoroalkylsulfonyl group anion salt to total moles of LiFSI and the lithium fluoroalkylsulfonyl group anion salt is less than ½.

10. The lithium secondary battery according to claim 9, wherein a total concentration of the LiFSI and the lithium fluoroalkylsulfonyl group anion salt is from 3 M to 20 M.

11. The lithium secondary battery of claim 6, wherein the cathode capable of intercalation and de-intercalation lithium ions comprises at least one compound selected from the group consisting of $LiMn_2O_4$, $LiCoO_2$, $LiFe_2(PO_4)$, $LiMn_{1/3}Ni_{1/3}Co_{1/3}O_2$, $LiNi_{0.5}Mn_{1.5}O_4$ and $LiCoPO_4$.

12. The lithium secondary battery of claim 6, wherein the anode capable of intercalation and de-intercalation of lithium ions is stable to water and has a redox potential greater than 0.5 V vs Li/Li+.

13. The lithium secondary battery of claim 6, wherein the anode capable of intercalation and de-intercalation of lithium ions comprises at least one compound selected from the group consisting of $Li_4Ti_5O_{12}$, elemental Sulfur, $Mo_6S_8$, $Cu_2V_2O_7$, $TiS_4$, $NbS_5$ and Li terephthalate.

14. A vehicle, comprising the lithium secondary battery of claim 6.

* * * * *